United States Patent
Arntz et al.

(10) Patent No.: US 10,633,476 B2
(45) Date of Patent: Apr. 28, 2020

(54) METHOD FOR PRODUCING A COMPOSITION COMPRISING POLYCARBODIIMIDE HAVING IMPROVED STORAGE STABILITY

(71) Applicant: Covestro Deutschland AG, Leverkusen (DE)

(72) Inventors: Hans-Detlef Arntz, Overath (DE); Stefan Wershofen, Mönchengladbach (DE); Ernst Felske, Neuss (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/551,369

(22) PCT Filed: Feb. 25, 2016

(86) PCT No.: PCT/EP2016/054010
§ 371 (c)(1),
(2) Date: Aug. 16, 2017

(87) PCT Pub. No.: WO2016/135256
PCT Pub. Date: Sep. 1, 2016

(65) Prior Publication Data
US 2018/0009929 A1      Jan. 11, 2018

(30) Foreign Application Priority Data
Feb. 26, 2015 (EP) .................................... 15156661

(51) Int. Cl.
| C08G 18/79 | (2006.01) |
| C07C 263/20 | (2006.01) |
| C08G 18/02 | (2006.01) |
| C08G 18/16 | (2006.01) |
| C08G 18/76 | (2006.01) |
| C07C 265/14 | (2006.01) |

(52) U.S. Cl.
CPC .......... C08G 18/025 (2013.01); C07C 263/20 (2013.01); C07C 265/14 (2013.01); C08G 18/168 (2013.01); C08G 18/7671 (2013.01); C08G 18/797 (2013.01)

(58) Field of Classification Search
CPC ................ C08G 18/025; C08G 18/168; C08G 18/7671; C08G 18/797; C07C 263/20; C07C 265/14
See application file for complete search history.

(56) References Cited

U.S. PATENT DOCUMENTS

| 3,516,950 A | 6/1970 | Haggis |
| 3,970,680 A | 7/1976 | Holland |
| 4,088,665 A | 5/1978 | Findeisen et al. |
| 5,202,358 A | 4/1993 | Scholl et al. |
| 6,120,699 A | 9/2000 | Narayan et al. |
| 7,714,148 B2 | 5/2010 | Wershofen et al. |
| 7,745,659 B2 | 6/2010 | Wershofen et al. |
| 7,825,276 B2 | 11/2010 | Wershofen et al. |
| 8,022,200 B2 | 9/2011 | Wershofen et al. |
| 9,353,221 B2 | 5/2016 | Avtomonov et al. |
| 2002/0052466 A1* | 5/2002 | Brahm .................. C07C 263/20 528/491 |
| 2005/0282993 A1* | 12/2005 | Rosthauser ........... C07C 263/20 528/59 |
| 2006/0128928 A1* | 6/2006 | Wershofen ........... C08G 18/025 528/49 |
| 2007/0167633 A1 | 7/2007 | Wershofen et al. |

FOREIGN PATENT DOCUMENTS

| JP | 06345707 A | * 12/1994 | |
| WO | WO-2006040912 A1 | * 4/2006 | .......... C07C 263/20 |
| WO | WO-2014044743 A1 | * 3/2014 | .......... C08G 18/025 |

OTHER PUBLICATIONS

JP-06345707-A, Dec. 1994_English Translation.*
WO-2006040912-A1, Apr. 2006, English Translation.*

* cited by examiner

*Primary Examiner* — Michael L Leonard
(74) *Attorney, Agent, or Firm* — Donald R. Palladino

(57) ABSTRACT

A method for producing a composition comprising polycarbodiimide, comprising the step of the reaction of a reaction mixture which contains an aromatic polyisocyanate and a carbodiimidising catalyst, wherein, before the reaction, the aromatic polyisocyanate is treated at a temperature of ≥80° C. to ≤150° C. and a pressure of ≥1 mbar to ≤500 mbar by passing through an inert gas and/or during the reaction, the reaction mixture is treated at a temperature of ≥80° C. to ≤150° C. and a pressure of ≥1 mbar to ≤500 mbar by passing through an inert gas and wherein the content of hydrolysable chlorine in the reaction mixture is ≤10 ppm.

12 Claims, No Drawings

METHOD FOR PRODUCING A COMPOSITION COMPRISING POLYCARBODIIMIDE HAVING IMPROVED STORAGE STABILITY

CROSS-REFERENCE TO RELATED APPLICATIONS

This application is a national stage application under 35 U.S.C. § 371 of PCT/EP2016/054010, filed Feb. 25, 2016, which claims the benefit of European Application No. 15156661.9, filed Feb. 26, 2015, both of which are being incorporated by reference herein.

The present invention relates to a process for producing a composition comprising polycarbodiimides, which comprises the step of reacting a reaction mixture comprising an aromatic polyisocyanate and a carbodiimidization catalyst.

BACKGROUND

In the catalytically assisted preparation of carbodiimides from aromatic polyisocyanates and in particular from 4,4'-diisocyanatodiphenylmethane (4,4'-MDI), the reactivity of the system can be subject to large fluctuations. This can be attributed at least partly to the content of hydrolyzable chlorine (HC) in the system. These reactivity fluctuations are frequently compensated for by adaptation of the catalyst concentration, with a phospholine oxide being used as catalyst in many cases. Although an increased phospholine oxide concentration influences the reaction rate in the desired way, it leads to a significant decrease in the product stability. The decrease in the product stability is revealed by an increase in the viscosity of the polycarbodiimide-containing composition.

There has in the past been no lack of attempts to reduce the content of hydrolyzable chlorine in the polyisocyanates. U.S. Pat. No. 3,516,950 is concerned with the production of rigid polyisocyanurate foams and in this context states that it is advantageous to use organic polyisocyanates which do not have an excessively high content of hydrolyzable chlorine. In order to reduce the HC content of the crude polyisocyanates, these can be treated with lime or other weakly basic materials. As an alternative, they can be heated to temperatures in the range from 150° C. to 220° C. while a stream of inert gas is passed through the liquid in order to assist the removal of hydrogen chloride. In one example, it is also described how crude MDI is heated to from 180° C. to 190° C. in a stream of nitrogen for 20 hours. It is reported that the NCO content is here reduced from 86.4% to 80.0% of the theoretical NCO content of MDI and the content of hydrolyzable chlorine decreases from 0.4% to 0.17%.

U.S. Pat. No. 4,088,665 relates to the partial carbodiimidization of monoisocyanates, diisocyanates and/or polyisocyanates in the presence of a phosphorus-organic compound specified there, followed by stopping of the carbodiimidization reaction by addition of a carbamoyl chloride or bromide. In one example, it is described how a reaction vessel is charged with 4,4'-MDI and flushed with nitrogen. After flushing, the contents are heated to 65° C. for one hour.

A general overview of the preparation of storage-stable carbodiimides may be found in DE 10 2004 033 849 A1. This patent application discloses processes for preparing organic isocyanates having carbodiimide and/or uretonimine groups by partial carbodiimidization of isocyanate groups using catalysts of the phospholine type, and subsequent stopping of the carbodiimidization reaction by addition of a silylated acid of the formula X—[Si(CH$_3$)$_3$]$_n$, where X in the formula is the neutral acid radical as is obtained by removal of the acidic hydrogen atoms from an n-basic acid having a pK$_a$ of not more than 3, with hydrohalic acids being excepted, and n is an integer of 1-3. In addition to the silylated acid, an unsilylated acid and/or an acid chloride and/or a sulfonic ester is added.

US 2005/0282993 A1 describes a process for preparing liquid storage-stable organic isocyanates having carbodiimide and/or uretonimine groups. Here, acidic impurities in the organic isocyanate are neutralized by means of an acid scavenger. A partial carbodiimidization is subsequently carried out in the presence of a catalyst of the phosphorus oxide type, followed by stopping of the carbodiimidization reaction by addition of an acid.

EP 1 971 623 B1 has the object of providing a simple and economical process for producing liquid, storage-stable and light-colored isocyanate mixtures having carbodiimide and/or uretonimine groups. The patent document discloses a process for preparing organic isocyanates having carbodiimide and/or uretonimine groups, in which one or more organic isocyanates having a Hazen color number of <100 APHA, preferably <50 APHA, are partially carbodiimidized using catalysts of the phospholine type and the carbodiimidization reaction is subsequently stopped, with the carbodiimidization being carried out in the presence of a silylated acid amide.

Advantages indicated are that the reactivity of the reaction mixture is increased and/or made uniform by the presence of a silylated acid amide during the carbodiimidization. In this way, the required reaction time is said to be able to be reduced or kept low and/or the required amount of catalyst be reduced. Both the isocyanates containing carbodiimide and/or uretonimine groups and the prepolymers prepared therefrom have, according to this patent document, good storage stability and a light color. The influence of the increased content of hydrolyzable chlorine on the reactivity or the reaction time is discussed with the aid of comparative examples 1 and 2. In examples 1 and 2 according to the patent, an improved reactivity is achieved compared to comparative example 2 and at the same concentration of catalyst used leads to shorter reaction times in examples 1 and 2 according to the patent.

EP 2 371 873 A1 relates to the production of polycarbodiimide and of aqueous dispersions of polycarbodiimide and describes a process for producing a composition comprising polycarbodiimides, which comprises the step of reacting a reaction mixture comprising an aliphatic or cycloaliphatic polyisocyanate and a carbodiimidization catalyst, characterized in that the reaction mixture is maintained at a temperature of from 160° C. to 230° C. during the reaction in the presence of 50-3000 ppm of carbodiimidization catalyst. Application of reduced pressure (500 mbar in the examples) or introduction of nitrogen or a combination of both features is said to be advantageous since the reaction gases are removed thereby and the carbodiimidization reaction is thus accelerated (paragraph [0011], examples). Even though the significantly milder reaction conditions for the reaction of aromatic isocyanates is indicated, it was not to be expected that the storage stability of partially carbodiimidized aromatic polyisocyanates can be improved by applying such a measure to the polyisocyanate before and/or during the reaction thereof.

EP 1 671 988 B1 describes, inter alia, carrying out the carbodiimidization reaction under nitrogen, which a person skilled in the art will understand to mean that the gas space above the liquid reaction mixture was filled up with nitrogen, which is not the same as passing a stream of nitrogen through the polyisocyanate before and/or during the reaction thereof.

WO 2007/076998 A1 discloses a process for preparing organic isocyanates having carbodiimide and/or uretonimine groups, in which one or more organic isocyanates having a Hazen color number of ≤100 APHA, preferably ≤50 APHA, are partially carbodiimidized using catalysts of the phospholine type and the carbodiimidization reaction is subsequently stopped. The carbodiimidization is carried out in the presence of at least one secondary or tertiary amine which contains at least one aliphatic or cycloaliphatic or araliphatic hydrocarbon radical which is optionally substituted and optionally contains heteroatoms. According to this patent application, the use of a secondary or tertiary amine which contains at least one aliphatic or cycloaliphatic or araliphatic hydrocarbon radical which is optionally substituted and optionally contains heteroatoms results in the reactivity of the starting isocyanate being increased.

This could, for example, be caused by the amines countering the reactivity-decreasing effect of potential HCl-eliminating secondary components in the starting isocyanate by acting as bases and binding HCl as hydrochloride. However, other mechanisms of action may also be possible.

As advantages of the process described, it is stated that the reactivity of the reaction mixture was increased and/or made uniform by the presence of a secondary or tertiary amine which contains at least one aliphatic or cycloaliphatic or araliphatic hydrocarbon radical which is optionally substituted and optionally contains heteroatoms during the carbodiimidization. In this way, the required reaction time is said to be able to be decreased or kept low and/or the required amount of catalyst be reduced. Both the isocyanates containing carbodiimide and/or uretonimine groups and the prepolymers prepared therefrom additionally have, according to the statements of this patent application, a good storage stability and a light color.

SUMMARY

It is an object of the present invention to provide a process for producing polycarbodiimide compositions, which makes do with relatively small amounts of starting materials remaining in the product and which nevertheless gives storage-stable (in the sense of a relatively low viscosity increase) polycarbodiimides.

According to the invention, the object is achieved by a process for producing a composition comprising polycarbodiimides, which comprises the step of reacting a reaction mixture comprising a polyisocyanate and a carbodiimidization catalyst, wherein the polyisocyanate is treated by passing an inert gas through it at a temperature of from ≥80° C. to ≤150° C. and a pressure of from ≥1 mbar to ≤500 mbar before the reaction and/or the reaction mixture is treated by passing an inert gas through it at a temperature of from ≥80° C. to ≤150° C. and a pressure of from ≥1 mbar to ≤500 mbar during the reaction, with, in addition, the content of hydrolyzable chlorine in the reaction mixture being ≤10 ppm.

DETAILED DESCRIPTION

It has been found that conditioning the polyisocyanate before or during its use in the production of the polycarbodiimides enables the content of hydrolyzable chlorine in the reaction system to be reduced. Without wishing to be tied to a theory, it is assumed that the desired increased storage stability is achieved as a result of a reduced content of the catalyst remaining in the end product. That relatively small amounts of catalyst can be used at all is in turn associated with the relatively small amount of acid, expressed as content of hydrolyzable chlorine, in the system.

The products obtained by the process of the invention can contain uretonimine groups in addition to carbodiimide groups. The content of free NCO groups can preferably be in the range from ≥27% by weight to ≤33% by weight.

Aromatic polyisocyanates are suitable for the process of the invention, with diisocyanates also being encompassed by the term "polyisocyanates".

Aromatic diisocyanates and polyisocyanates such as tolylene diisocyanate and diisocyanates and polyisocyanates of the diphenylmethane series are particularly suitable. Particular mention may be made of:

aromatic diisocyanates such as 2,4- and/or 2,6-diisocyanatotoluene (TDI), 2,2'-, 2,4'- and/or 4,4'-diisocyanatodiphenylmethane (MDI) or any mixtures of such aromatic diisocyanates, diisocyanate and polyisocyanate mixtures of the diphenylmethane series having a content of monomeric diisocyanatodiphenylmethane isomers of from 80 to 100% by weight and a content of more than bifunctional polyisocyanates of the diphenylmethane series of from 0 to 20% by weight, where the diisocyanatodiphenylmethane isomers are made up of from 0 to 100% by weight of 4,4'-diisocyanatodiphenylmethane, from 100 to 0% by weight of 2,4'-diisocyanatodiphenylmethane and from 0 to 8% by weight of 2,2'-diisocyanatodiphenylmethane, where the percentages mentioned add up to 100% by weight.

Possible catalysts for the process of the invention are, in particular, organic phosphorus oxides.

The temperatures for the treatment of the polyisocyanate or the reaction mixture are, according to the invention, in each case from ≥80° C. to ≤150° C. A preferred temperature range is in each case and independently from ≥85° C. to ≤120° C., more preferably from ≥90° C. to ≤100° C.

The pressures for the treatment of the polyisocyanate or the reaction mixture are, according to the invention, in each case from ≥1 mbar to ≤500 mbar. A preferred pressure range is in each case and independently from ≥1 mbar to ≤300 mbar, more preferably from ≥1 mbar to ≤100 mbar.

As a result of the comparatively low temperatures during the treatment, no appreciable distillation of the polyisocyanate occurs even at a pressure of 1 mbar. Furthermore, undesirable thermal secondary reactions of the polyisocyanate are avoided. The polyisocyanate which has been pretreated according to the invention can thus be used without further work-up or purification in a carbodiimidization reaction. The same applies when the reaction mixture is treated according to the invention during the reaction to form the carbodiimide.

When the route in which the polyisocyanate is treated according to the invention only before commencement of the carbodiimidization reaction is selected, the actual carbodiimidization reaction can of course be carried out under the conditions customary for this reaction, as indicated, for example, in EP 1 671 988 B1 or EP 1 820 796 B1. The carbodiimidization reaction can be carried out either under reduced pressure, at atmospheric pressure or under a slightly superatmospheric pressure.

The third element of the treatment according to the invention is, in addition to the particular temperature range and the particular pressure range, that an inert gas is passed through the polyisocyanate or through the reaction mixture during the treatment. Possible inert gases are, in particular, noble gases such as argon and also nitrogen. It is assumed that the inert gas can transport gaseous hydrogen chloride away, which results in a decrease in the content of hydrolyzable chlorine in the polyisocyanate or the reaction mixture.

The passing-through of the inert gas can, for example, be achieved by means of a gas-introducing stirrer or by means of a sieve tray in a reaction vessel.

Furthermore, the content of hydrolyzable chlorine ("HC content") in the reaction mixture is ≤10 ppm in the process of the invention. The content is preferably from ≥0.1 ppm to ≤10 ppm, more preferably from ≥1 ppm to ≤5 ppm. This can be brought about by the above-described treatment of the polyisocyanate.

The determination of the content of hydrolyzable chlorine in isocyanates is carried out by urethanization, hydrolysis and potentiometric titration with silver nitrate using a silver/silver chloride combination electrode. For example, in the case of MDI, the HC value is determined by reaction of MDI with lower alcohols such as methanol (see ASTM D5523-94 for monomeric MDI or ASTM 5629-99 or 6099-03 for polymeric MDI).

Specific embodiments of the present invention are indicated below. They can be combined in any way, unless the contrary is clear from the context.

In one embodiment of the process of the invention, the content of the carbodiimidization catalyst in the reaction mixture is ≤5 ppm, preferably <3.5 ppm, particularly preferably <3 ppm. The content here is the proportion by weight of the catalyst, based on the total weight of the reaction mixture. Such low catalyst contents are possible because of the low HC content in the reaction mixture. Accordingly, the content of catalyst remaining in the end product, which catalyzes undesirable secondary reactions during storage, is also lower. The storage stability then increases. Preference is given to a catalyst content of from ≥0.1 ppm to ≤2.5 ppm, more preferably from ≥0.5 ppm to ≤1.5 ppm.

In a further embodiment of the process of the invention, the polyisocyanate is diphenylmethane diisocyanate. Preference is given here to 4,4'-MDI.

In a further embodiment of the process of the invention, the carbodiimidization catalyst is a phospholine oxide. Such catalysts are known, for example, from EP 515 933 A1 and U.S. Pat. No. 6,120,699. Typical examples of these catalysts are:

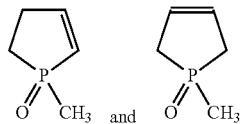

Further examples are 1-phenyl-1-oxo-1-phosphacyclopent-2-ene and 1-phenyl-1-oxo-1-phosphacyclopent-3-ene. An industrial mixture of 1-methyl-1-oxo-1-phosphacyclopent-2-ene and 1-methyl-1-oxo-1-phosphacyclopent-3-ene or an industrial mixture of 1-phenyl-1-oxo-1-phosphacyclopent-2-ene and 1-phenyl-1-oxo-1-phosphacyclopent-3-ene is also suitable.

In a further embodiment of the process of the invention, the reaction occurs in the absence of an acid scavenger. Due to the low HC content, an acid scavenger is not necessary. Acid scavengers which are excluded are, in particular, bases such as lime or epoxides.

In a further embodiment of the process of the invention, a stopper is added to the product obtained after the end of the reaction of the reaction mixture. This stopper deactivates the catalyst. Compounds suitable as stoppers are, for example, trifluoromethanesulfonic esters, trimethylsilyl triflate and other carbon-based or inorganic acids. This stopper is preferably used in association with a phospholine oxide catalyst. A preferred stopper is ethyl triflate.

The trifluoromethanesulfonic ester is preferably added in an amount of from ≥10 ppm to ≤100 ppm, more preferably from ≥15 ppm to ≤50 ppm. The content here is the proportion by weight of the stopper, based on the total weight of the reaction mixture.

In a further embodiment of the process of the invention, no acid scavenger is added to the product obtained after the end of the reaction of the reaction mixture. Due to the low HC content, an acid scavenger is also not necessary in the end product. Excluded acid scavengers are, in particular, bases such as lime or epoxides.

In a further embodiment of the process of the invention, a polyisocyanate is added to the product obtained after the end of the reaction of the reaction mixture. Carbodiimide-containing isocyanate blends can be produced in this way. Isocyanates added can be identical to or different from the aromatic polyisocyanate(s) used for the carbodiimidization. As representatives of aliphatic and/or cycloaliphatic diisocyanates, mention may be made by way of example of isophorone diisocyanate, hexamethylene diisocyanate and dicyclohexylmethane diisocyanate (in each case the pure isomers or any isomer mixtures). As representatives of araliphatic diisocyanates, mention may be made by way of example of the various isomers of xylidene diisocyanates.

Aromatic diisocyanates and polyisocyanates such as tolylene diisocyanate and diisocyanates and polyisocyanates of the diphenylmethane series are particularly suitable. Particular mention may be made of aromatic diisocyanates such as 2,4- and/or 2,6-diisocyanatotoluene (TDI), 2,2'-, 2,4'- and/or 4,4'-diisocyanatodiphenylmethane (MDI) and any mixtures of such aromatic diisocyanates; also diisocyanate and polyisocyanate mixtures of the diphenylmethane series having a content of monomeric diisocyanatodiphenylmethane isomers of from 80 to 100% by weight and a content of more than bifunctional polyisocyanates of the diphenylmethane series of from 0 to 20% by weight, where the diisocyanatodiphenylmethane isomers are made up of from 0 to 100% by weight of 4,4'-diisocyanatodiphenylmethane, from 100 to 0% by weight of 2,4'-diisocyanatodiphenylmethane and from 0 to 8% by weight of 2,2'-diisocyanatodiphenylmethane, where the percentages mentioned add up to 100% by weight.

In a further embodiment of the process of the invention, the product obtained from the reaction of the reaction mixture is reacted with a polyol after the end of the reaction. Carbodiimide-containing prepolymers can be obtained in this way. Suitable polyols are both simple polyhydric alcohols having a molecular weight in the range from 62 to 599 g/mol, preferably from 62 to 300 g/mol, e.g. ethylene glycol, trimethylolpropane, 1,2-propanediol, 1,2-butanediol or 2,3-butanediol, hexanediol, octanediol, dodecanediol and/or octadecanediol, but in particular relatively high molecular weight polyether polyols and/or polyester polyols of the type known per se from polyurethane chemistry which have molecular weights of from 600 to 8000 g/mol, preferably from 800 to 4000 g/mol, and have at least two, generally from 2 to 8, preferably from 2 to 4, primary and/or secondary hydroxyl groups.

EXAMPLES

The present invention is illustrated by the following examples, but without being restricted thereto. The terms used in the examples have the following meanings:

44M: diphenylmethane 4,4'-diisocyanate (NCO content: 33.6% by weight)

PHO: phospholine oxide (carbodiimidization catalyst); industrial mixture of 1-methyl-1-oxo-1,5-phosphacyclopent-2-ene and 1-methyl-1-oxo-1-phosphacyclopent-3-ene, 1 percent strength by weight solution in toluene ETF: ethyl triflate (stopper); ethyl trifluoromethanesulfonate To determine the content of hydrolyzable chlorine (HC value), the isocyanate sample was admixed with methanol and urethanized under reflux for 10 minutes. The mixture was subsequently hydrolyzed after dilution with water by boiling under reflux. The ionogenic chlorine formed here was, after acidification with nitric acid and standard addition of a known mass of sodium chloride, titrated argentometrically with a silver nitrate standard solution. The titration was carried out drift-controlled (equilibrium titration) with incremental introduction of reagent and automatic equivalence point evaluation. The content of hydrolyzable chlorine was calculated, taking into account the standard addition, from the initial weight of isocyanate sample and the consumption of silver nitrate standard solution.

The viscosity was determined by means of a Physika MCR 51 rheometer from Anton Paar, Ostfildern, DE at a shear rate of 500-5000 1/s at 25° C.

The NCO content of the reaction product was determined in accordance with DIN EN 1242.

Example 1: Effect of Various Treatments of 44M on the HC Value

Samples of the same batch of 44M were subjected to the treatments indicated in the following table:

| Example No. | 1-1 (comparison) | 1-2 (comparison) | 1-3 (according to the invention) |
| --- | --- | --- | --- |
| HC value before treatment | 17 ppm | 17 ppm | 17 ppm |
| Treatment | none | 100° C., 1 mbar vacuum, 2 hours duration | 100° C., 1 mbar vacuum, passing-through of nitrogen, 2 hours duration |
| HC value after treatment | 17 ppm | 11 ppm | 5 ppm |

Example 2: Production of Carbodiimide Compositions

General Method:

10 kg of technical-grade 44M, which contained 750 ppm of 3,5-di-tert-butyl-4-hydroxytoluene, were heated to about 90° C. under $N_2$ with stirring. The amount of catalyst indicated in the following table was subsequently added. The reaction mixture was heated to about 95° C. under $N_2$ with stirring until the desired NCO content had been attained. The carbodiimidization was then stopped by addition of the stopper ETF and the mixture was stirred further for 1 hour.

For better comparability, the carbodiimide was produced using a PHO concentration which was adapted so that the reactions had very similar rates and could be ended after 4.5 hours.

| Example No. | 2-1 (comparison) | 2-2 (comparison) | 2-3 (according to the invention) |
| --- | --- | --- | --- |
| 44M sample from example | 1-1 | 1-2 | 1-3 |
| HC value of the 44M | 17 ppm | 17 ppm | 5 ppm |
| PHO content | 4 ppm | 4 ppm | 1 ppm |
| ETF content | 50 ppm | 200 ppm | 50 ppm |
| Molar ratio of ETF:PHO | 8.1 | 32.6 | 32.6 |
| Viscosity | 30 mPa · s | 30 mPa · s | 33 mPa · s |
| NCO content | 29.6% by weight | 29.6% by weight | 29.5% by weight |

Example 3: Storage Tests

The samples obtained from example 2 were subjected to simulated accelerated storage by heating to 100° C. for three days. Viscosity and NCO content were subsequently determined again.

| Example No. | 3-1 (comparison) | 3-2 (comparison) | 3-3 (according to the invention) |
| --- | --- | --- | --- |
| Sample from example | 2-1 | 2-2 | 2-3 |
| Viscosity | 82 mPa · s | 65 mPa · s | 58 mPa · s |
| NCO content | 26.9% by weight | 27.7% by weight | 28.5% by weight |

Under the drastic storage conditions of 100° C. for three days, it was found that the stability of the composition produced according to the invention is best, recognizable by the smallest increase in the viscosity and the smallest decrease in the NCO content, even at the same high ETF:PHO ratio.

The invention claimed is:

1. A process for producing a composition comprising polycarbodiimides, which comprises the step of reacting a reaction mixture comprising an aromatic polyisocyanate and a carbodiimidization catalyst, wherein the content of hydrolyzable chlorine in the reaction mixture is brought to ≤10 ppm by a treatment comprising:

passing an inert gas comprising a noble gas or nitrogen through the aromatic polyisocyanate before the reaction, wherein the treatment of the aromatic polyisocyanate is at a temperature of from ≥80° C. to ≤120° C. and a pressure of from ≥1 mbar to ≤500 mbar, and/or passing an inert gas comprising a noble gas or nitrogen through the reaction mixture during the reaction, wherein the treatment of the reaction mixture is at a temperature of from ≥80° C. to ≤120° C. and a pressure of from ≥1 mbar to ≤500 mbar, and wherein the content of carbodiimidization catalyst in the reaction mixture is ≤1.5 ppm.

2. The process of claim 1 wherein the aromatic polyisocyanate is diphenylmethane diisocyanate.

3. The process of claim 1, wherein the carbodiimidization catalyst is a phospholine oxide.

4. The process of claim 1, wherein the reaction is carried out in the absence of an acid scavenger.

5. The process of claim 1, wherein a stopper is added to the composition obtained after the end of the reaction of the reaction mixture.

6. The process as claimed in claim 5, wherein the stopper comprises trifluoromethanesulfonic ester and the trifluoromethane sulfonic ester is added in an amount of from ≥10 ppm to ≤100 ppm.

7. The process of claim 1, wherein no acid scavenger is added to the composition obtained after the end of the reaction of the reaction mixture.

8. The process of claim 1, wherein a polyisocyanate is added to the composition obtained after the end of the reaction of the reaction mixture.

9. The process of claim 1, wherein the polycarbodiimides obtained from the reaction of the reaction mixture is reacted with a polyol after the end of the reaction.

10. The process of claim 1, wherein the content of the carbodiimidization catalyst in the reaction mixture is ≥0.5 ppm to ≤1.5 ppm.

11. The process of claim 6, wherein the trifluoromethane sulfonic ester is added in an amount of 50 ppm to 100 ppm.

12. The process of claim 1, wherein the composition comprising polycarbodiimides has a content of free NCO groups of ≥27% by weight to ≤33% by weight.

* * * * *